(12) United States Patent
Laufer

(10) Patent No.: US 10,864,014 B2
(45) Date of Patent: *Dec. 15, 2020

(54) METHODS AND DEVICES FOR DIASTOLIC ASSIST

(71) Applicant: CORDYNAMIX, INC., Menlo Park, CA (US)

(72) Inventor: Michael D. Laufer, Menlo Park, CA (US)

(73) Assignee: CORDYNAMIX, INC., Menlo Park, CA (US)

(*) Notice: Subject to any disclaimer, the term of this patent is extended or adjusted under 35 U.S.C. 154(b) by 454 days.

This patent is subject to a terminal disclaimer.

(21) Appl. No.: 15/373,136

(22) Filed: Dec. 8, 2016

(65) Prior Publication Data

US 2017/0164968 A1 Jun. 15, 2017

Related U.S. Application Data

(60) Provisional application No. 62/265,424, filed on Dec. 10, 2015.

(51) Int. Cl.
| | |
|---|---|
| *A61B 18/14* | (2006.01) |
| *A61B 17/3211* | (2006.01) |
| *A61B 6/12* | (2006.01) |
| *A61B 90/00* | (2016.01) |
| *A61B 17/32* | (2006.01) |

(Continued)

(52) U.S. Cl.
CPC ............ *A61B 17/3211* (2013.01); *A61B 6/12* (2013.01); *A61B 6/487* (2013.01); *A61B 17/320016* (2013.01); *A61B 18/1492* (2013.01); *A61B 90/06* (2016.02); *A61B 90/39* (2016.02); *A61B 17/3209* (2013.01); *A61B 2017/00044* (2013.01); *A61B 2017/00243* (2013.01); *A61B 2017/00247* (2013.01);

(Continued)

(58) Field of Classification Search
CPC ...... A61B 17/00234; A61B 17/320016; A61B 17/3209; A61B 17/3211; A61B 18/1492; A61B 2017/00044; A61B 2017/00243; A61B 2017/00247; A61B 2017/00477; A61B 2017/00862; A61B 2017/22071; A61B 2018/00077; A61B 2018/00083; A61B 2018/00172; A61B 2018/00351; A61B 2018/00589; A61B 2018/00595; A61B 2018/00601; A61B 2018/00827; A61B 2018/00839; A61B 2018/00892; A61B 2018/00904; A61B 2018/1412; A61B 2018/1475; A61B 2090/064; A61B 2090/3966; A61B 6/12; A61B 6/487; A61B 90/06; A61B 90/39; A61N 1/056

See application file for complete search history.

(56) References Cited

U.S. PATENT DOCUMENTS

| | | | | |
|---|---|---|---|---|
| 4,232,676 A | * | 11/1980 | Herczog | ............. A61B 18/14 |
| | | | | 606/48 |
| 5,449,355 A | * | 9/1995 | Rhum | ................. A61K 45/06 |
| | | | | 606/41 |

(Continued)

*Primary Examiner* — Michael F Peffley
*Assistant Examiner* — Amanda L Zink
(74) *Attorney, Agent, or Firm* — Levine Bagade Han LLP

(57) ABSTRACT

The devices and method described herein allow for therapeutic damage to increase volume in these hyperdynamic hearts to allow improved physiology and ventricular filling and to reduce diastolic filling pressure by making the ventricle less stiff.

21 Claims, 8 Drawing Sheets

(51) Int. Cl.
*A61B 6/00* (2006.01)
*A61B 18/00* (2006.01)
*A61B 17/00* (2006.01)
*A61B 17/22* (2006.01)
*A61B 17/3209* (2006.01)
*A61N 1/05* (2006.01)

(52) U.S. Cl.
CPC ............ *A61B 2017/00477* (2013.01); *A61B 2017/00862* (2013.01); *A61B 2017/22071* (2013.01); *A61B 2018/00077* (2013.01); *A61B 2018/00083* (2013.01); *A61B 2018/00172* (2013.01); *A61B 2018/00351* (2013.01); *A61B 2018/00589* (2013.01); *A61B 2018/00595* (2013.01); *A61B 2018/00601* (2013.01); *A61B 2018/00827* (2013.01); *A61B 2018/00839* (2013.01); *A61B 2018/00892* (2013.01); *A61B 2018/00904* (2013.01); *A61B 2018/1412* (2013.01); *A61B 2018/1475* (2013.01); *A61B 2090/064* (2016.02); *A61B 2090/3966* (2016.02); *A61N 1/056* (2013.01)

(56) References Cited

U.S. PATENT DOCUMENTS

| | | | | |
|---|---|---|---|---|
| 5,626,595 | A * | 5/1997 | Sklar | A61B 17/320016 606/170 |
| 5,658,301 | A * | 8/1997 | Lemaitre | A61B 17/32075 606/159 |
| 6,770,071 | B2 * | 8/2004 | Woloszko | A61B 18/1402 606/41 |
| 7,887,556 | B2 * | 2/2011 | Simpson | A61B 17/320758 606/159 |
| 8,551,129 | B2 * | 10/2013 | Lary | A61B 17/320016 606/159 |
| 2010/0268175 | A1 * | 10/2010 | Lunsford | A61B 17/320725 604/272 |
| 2012/0296153 | A1 | 11/2012 | Laufer et al. | |
| 2015/0065872 | A1 * | 3/2015 | Drake | A61M 5/007 600/432 |
| 2015/0094715 | A1 | 4/2015 | Laufer et al. | |
| 2016/0206345 | A1 * | 7/2016 | Laufer | A61B 18/1492 |
| 2017/0042565 | A1 * | 2/2017 | Ellsworth | A61B 17/320036 |

* cited by examiner

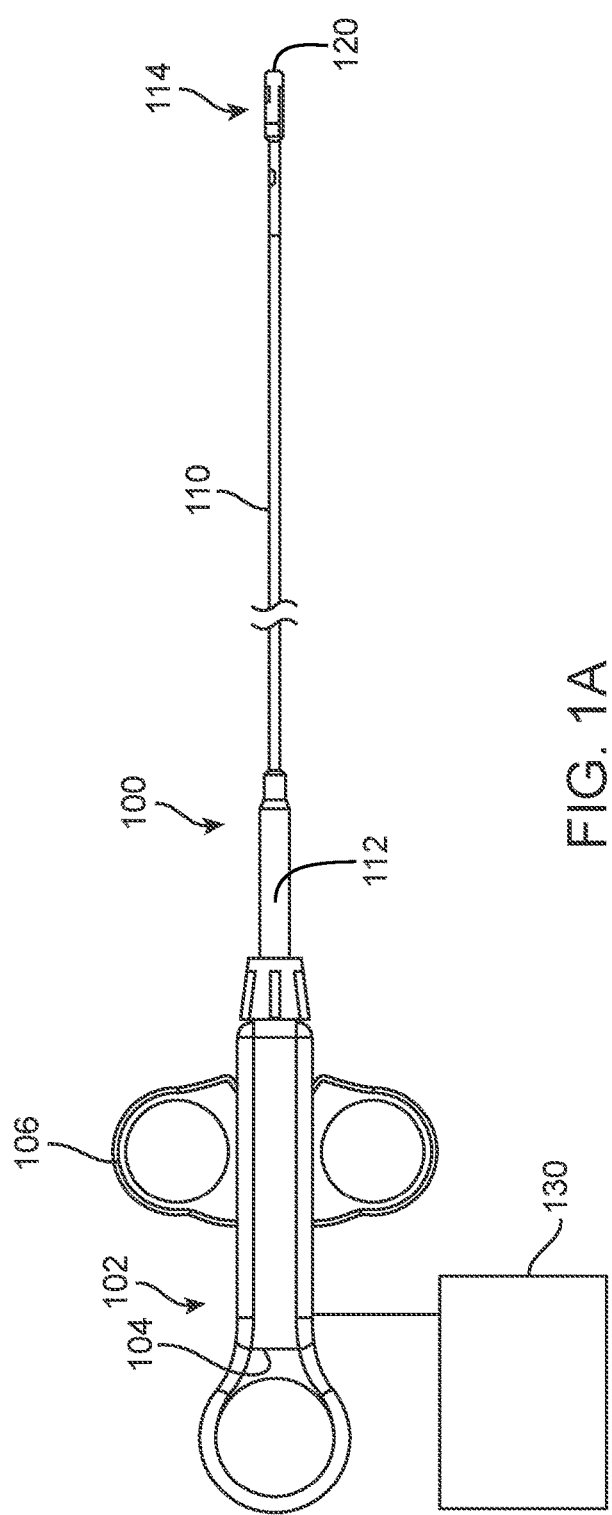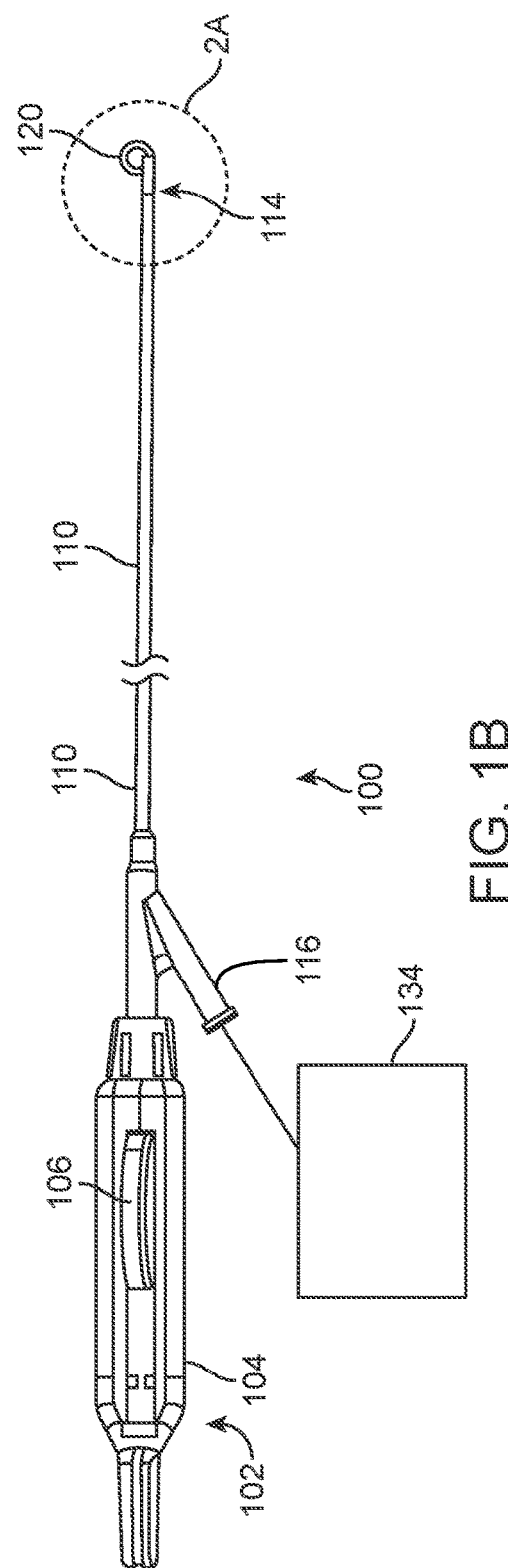
FIG. 1A
FIG. 1B

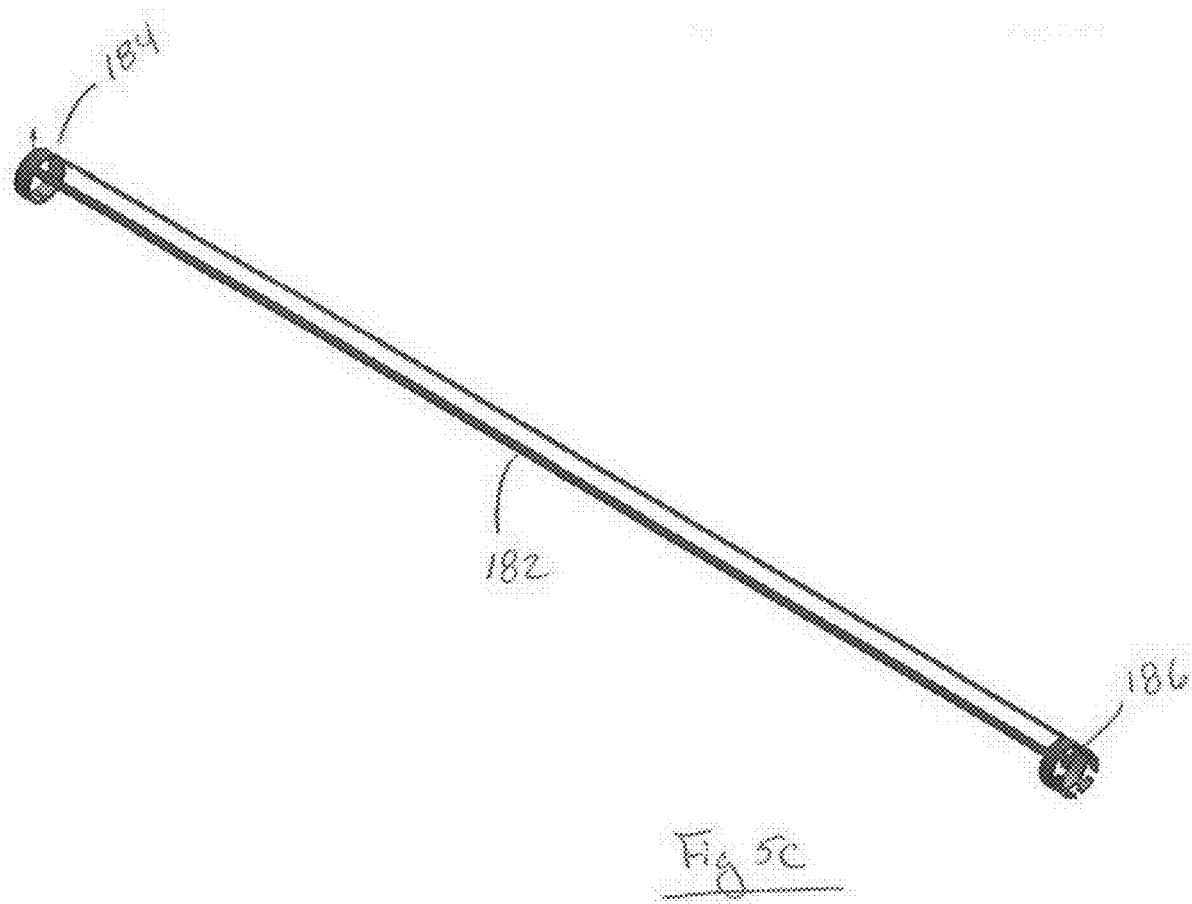

METHODS AND DEVICES FOR DIASTOLIC ASSIST

CROSS-REFERENCE TO RELATED APPLICATIONS

This is a non-provisional of U.S. Provisional Application 62/265,424 filed on Dec. 10, 2016, the entirety of which is incorporated by reference. This application also incorporates by reference: U.S. Provisional Application 61/911,456 filed on Dec. 3, 2013; and U.S. patent application Ser. No. 14/152,189 filed on Jan. 10, 2014.

BACKGROUND OF THE INVENTION

Congestive heart failure (CHF) in the U.S. has a prevalence of approximately 5.8 million people and an incidence of approximately 550,000 people annually. CHF is a rapidly growing medical problem, CHF can be categorized as either systolic heart failure (SHF) or diastolic heart failure (DHF). The estimated direct and indirect cost of CHF in the United States for 2009 is $37.2 billion. CHF is the primary reason for 12-15 million office visits and 6.5 million hospital days each year. CHF is also thought to be the cause of at least 20 percent of all hospital admissions among patients older than 65. Over the past decade, the rate of hospitalizations for heart failure has increased by 159 percent. About half of all patients with CHF have DHF. DHF has an annual mortality of ~10%.

The hearts of patients with diastolic dysfunction can contract normally or even with hyperdynamic function. However, in patients experiencing DHF, the part of the cardiac cycle that involves diastole is abnormal as the left ventricle cannot relax or expand sufficiently. The inability of the left ventricle to fully relax results in sub-optimal filling of the left ventricle with blood.

In particular, diastolic dysfunction is determined by two factors: 1) active myocardial relaxation, primarily affecting early diastole; or 2) passive elasticity or distensibility of the left ventricle, primarily affecting late diastole.

The abnormal filling of the ventricles in DHF results in limited cardiac output, especially during exertion. As a result, for any given ventricular volume in a heart with DHF, ventricular pressures are elevated, with backup in the circulatory system, leading to pulmonary congestion and edema identical to those seen in patients with SHF. Symptomatically, patients may immediately feel short of breath. This dysfunction can ultimately lead to multi-organ dysfunction and death.

There are currently no approved devices for diastolic dysfunction. Additionally, pharmaceutical intervention has not yet shown to improve outcomes in this population.

BRIEF SUMMARY OF THE INVENTION

The present disclosure includes devices and methods to increase volume in these hyperdynamic hearts to allow improved physiology and ventricular filling and to reduce diastolic filling pressure. For example, the treatments described herein, when performed in a diseased heart, can result in the heart chamber filling to an increased volume of blood (as compared to pre-treatment volumes) at the same pressure. Thereby, the chamber can move more volume than it could pre-treatment.

In a first variation, the disclosure includes a method of improving a diastolic heart function in a heart of a patient having diastolic heart dysfunction. One variation of the method includes positioning a medical device within a body of the patient; advancing the medical device into an interior chamber of the heart; creating at least one incision in cardiac muscle forming an interior heart wall of the interior chamber without cutting through the exterior part of said heart wall, where the incision is sufficient to reduce a stiffness of the interior chamber to increase volume of the chamber and reduce diastolic filling pressure.

The above method can further include creating a plurality of incision. The plurality of incision can comprise at least one hole in the cardiac muscle or can comprise creating a plurality of incision.

Typically, the method includes creating at least one incision without reducing integrity of the cardiac muscle.

Access to the heart can occur via a vascular approach, an open surgical approach, or a thoracoscopic approach. Furthermore, advancing the medical device can comprise advancing the medical device into the interior chamber of the heart via a transapical approach.

The devices used to create the therapeutic injury can include any devices selected from the group consisting of a blade, a mechanical cutting device, an electrosurgical device, and a laser device.

In some variations, the methods occur by inducing tachycardia of the heart. Furthermore, incisions can be created on an interior of the heart.

The devices can be secured to cardiac muscle prior to or during creating the incision.

The methods and devices can also optionally deliver bioactive agent at least one incision to modify the healing process of the cardiac muscle.

Another variation of the method includes a method of increasing blood flow in a diseased heart. One such example includes positioning a medical device within a body of the patient; advancing the medical device into an interior chamber of the heart; locating a target area of heart tissue; and creating at least one incision in cardiac muscle of the heart tissue to decrease the stiffness of the interior chamber to permit the interior chamber to increase in volume during diastole. One variation of the device used to make the one or more incisions mentioned above includes a soft semicircular tip at the distal end of the device that may be in fluid communication with an injection port outside the patient. The tip can be imaged when inside the heart under x-ray fluoroscopic imaging or any other type of imaging or virtual tracking. When the tip is placed into the area of the apex of the heart, the tip configuration changes and the change can be seen during imaging. A contrast imaging agent may be injected through the tip when injected outside the patient through the injection port. Said contrast agent flows into the ventricle. The pattern of flow gives information to the user as to where the cutting member is relative to the inside wall of the ventricle. When the cutting member is adjacent to or embedded in the muscle of the heart wall, the contrast agent will flow only to the surface of the inside wall while the cutting element will be seen within that wall. The contrast agent can also be seen within the cat made in the heart wall.

Another variation of the methods includes methods of increasing blood flow in a diseased heart by advancing a device within a left ventricle of the heart; placing an elastic member within the left ventricle such that upon diastole the elastic member expands with the left ventricle. The elastic member has one or more arms. At least one of these arms may have a cutting member. The cutting member may be moved along the inside of the ventricle wall making a controlled incision therein. The depth of the incision is controlled by the distance between the arm and/or elastic member and the tip of the cutting member. If several cutting members are included, these members may be moved individually or together by a cable or other coupled member connecting the cutting member to an actuator outside of the patient to increase a volume within the left ventricle so as to increase blood flow therein.

The elastic member can comprise a plurality of elastic members positioned in a substantially concentric pattern within the left ventricle. Alternatively, or in combination, the elastic member can comprise at least one spirally shaped elastic member positioned in a substantially concentric pattern within the left ventricle.

The present disclosure also includes variations of medical devices for creating the elongated incisions within soft tissue. In one example the device comprises a handle comprising a handle body and an actuating member; a flexible shaft having a near end coupled to the handle body and a far end, the flexible shaft; an atraumatic tip located at the far end; a cutting member pivotally secured within the flexible shaft and having a cutting edge; and a linking member coupling the actuating member of the handle to the cutting member, wherein when the actuating member applies a tensile force to the linking member, the cutting member pivots to a lateral side of the flexible shaft to expose the cutting surface and allow cutting of the soft tissue, the tensile force also causing biasing of the far end of flexible shaft towards the lateral side to assist in maintaining the cutting surface within the soft tissue.

A variation of the device includes a channel extending between the near end of the flexible shaft through the opening. In addition, the medical device can further include a sheath being slidably located on the flexible shaft, where the sheath can be advanced to cover the opening and retracted to expose the opening.

Variations of the medical device can include a cutting member that comprises an electrically non-conductive material. In such cases, the cutting member can optionally include at least one electrode located on the electrically non-conductive material, where the at least one electrode is electrically coupleable to a source of electrical current.

In alternate variations, the cutting member comprises an electrically conductive material and where the cutting member is electrically coupleable to a source of electrical current.

The devices described herein can have one or more openings adjacent to the far end of the flexible shaft, where the cutting surface of the cutting member extends through the opening when pivoted. In some variations, the device further comprises one or more electrodes adjacent to the opening.

The devices described herein can further include a rigid section at the far end of the flexible shaft where the rigid section comprises an opening through which the cutting surface of the cutting member extends when pivoted. As discussed herein, the rigid section at the far end of the device provides uniformity to create the incision, while the flexible nature of the shaft permits navigation to remote tissues through tortuous anatomy.

The devices described herein can include an atraumatic tip located at the far end of the flexible shaft. The atraumatic tip can comprise a curved elastic member or any shape that provides a lateral force to assist the cutting member to penetrate tissue. Alternatively, the atraumatic tip can simply comprise a blunt elastic or inelastic material. Variations of the devices can include atraumatic tips that are radiopaque.

Furthermore, the devices described herein can employ any additional number of lumens for fluid delivery, guidewire advancement, imaging, etc.

This application is related to U.S. Publication No. 2012/0296153 U.S. patent application Ser. No. 13/277,158 filed on Oct. 19, 2011 and U.S. Provisional Application Nos. 61/394,759 filed on Oct. 19, 2010; 61/478,495 filed on Apr. 23, 2011; 61/504,641 filed on Jul. 5, 2011; 61/884,332 filed on Sep. 30, 2013; and 61/911,456 filed on Dec. 12, 2013, the contents of which are each incorporated herein by reference in its entirety.

BRIEF DESCRIPTION OF THE SEVERAL VIEWS OF THE DRAWINGS

FIGS. 1A and 1B illustrate respective top and side views of a first example of a treatment device that can be used to make incisions in soft tissue according to the present disclosure.

FIG. 5C illustrates a variation of a strut assembly that is positionable in the shaft of the device at the working ends far end.

DETAILED DESCRIPTION OF THE INVENTION

Figure 2A:
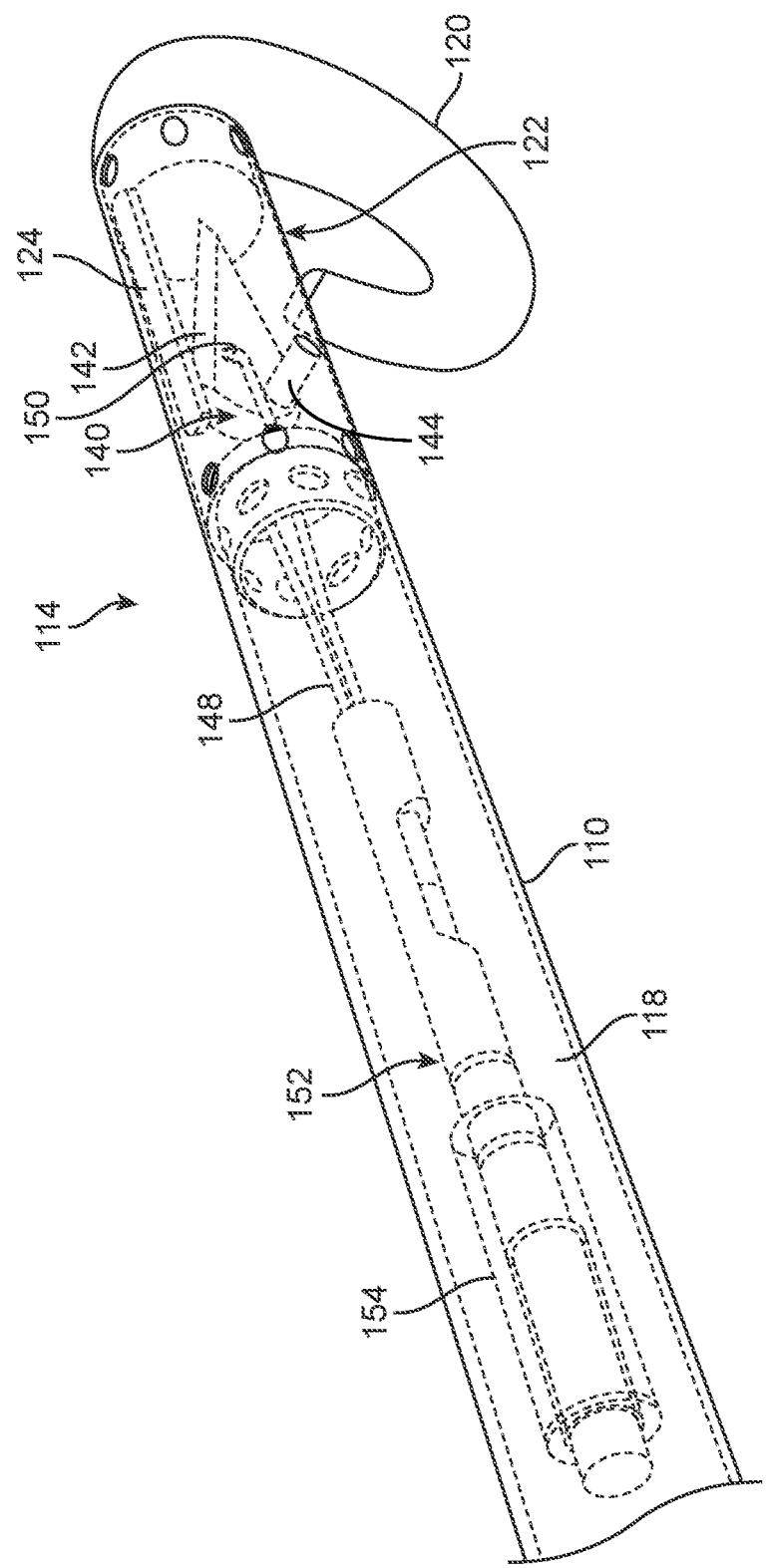
FIG. 2A illustrates perspective partial cross sectional view of a far end of the device of FIGS. 1A and 1B.

The illustrations described herein are examples of the invention. Because of the scope of the invention, it is specifically contemplated that combinations of aspects of specific embodiments or combinations of the specific embodiments themselves are within the scope of this disclosure.

As noted above, the methods described herein increase a volume of a chamber of a heart to improve blood flow in diastolic heart failure. For example, incisions, cuts, holes, or other separation of tissue can be made in muscle forming the wall of the left ventricle to improve a diastolic function of the heart. Although the description and claims described herein discuss primarily treatments occurring in a left ventricle, unless specifically discussed or claimed, the treatments can occur in any chamber of the heart (e.g., the atriums and/or ventricles). Typically, access to the chambers of the heart (endocardium) can be made percutaneously or via a transapical approach. Once in the ventricle, small cuts, holes, or a combination thereof are made to the cardiac muscle at one or more layers of the musculature.

One of the goals of the therapeutic damage is to increase volume in these hyperdynamic hearts to allow improved physiology and ventricular filling and to reduce diastolic filling pressure by making the ventricle less stiff. In some cases, the type of therapeutic damage, e.g., angles, dimensions, length, depth, density, and architecture shall balance of the integrity of the musculature versus the functional result. Meaning the amount of therapeutic damage to the tissue must be balanced against compromising the integrity of the tissue. In many cases, the treatment can be optimized to ensure adequate function physiologically, hemodynamically, and electrophysiologically. Unless otherwise specified, the therapeutic treatments only extend into one or more layers of the cardiac muscle and not through the wall of the heart.

The therapeutic damage caused to the cardiac muscle can be additionally treated with agents that prevent closure of the wounds. Such agents can include pyrolitic carbon, titanium-nitride-oxide taxanes, fibrinogen, collagen, thrombin, phosphorylcholine, heparin, rapamycin, radioactive 188Re and 32P, silver nitrate, dactinomycin, sirolimus everolimus, Abt-578, tacrolimus, camptothecin, etoposide, vincristine, mitomycin, fluorouracil, or cell adhesion peptides. Taxanes include, for example, paclitaxel, 10-deacetyltaxol, 7-epi-10-deacetyltaxol, 7-xylosyl-10-deacetyltaxol, cephalomannine, baccatin III, baccatin V, 10-deacetylbaccatin III, 7-epi-10-deacetylbaccatin III, docetaxel. Other agents that could effect improved function include bioactive substances including proteins and cells like stem cells.

FIGS. 1A and 1B, illustrate respective top and side views of a first example of a treatment device 100 that can be used to make incisions in soft tissue according to the present disclosure. As shown, the device includes a handle 102 comprising a handle body 104 and an actuating member 106. Variations of the device can include handles of any number of configurations. Typically, such variations include an actuating member that is moveable relative to a handle body. Such examples can include triggers, levers, dials, etc. Furthermore, the actuating portion can include a switch type mechanism in the event the respective variation is driven by a motor or other automated means.

The device 100 further includes a flexible shaft 110 that extends between a near end 112 and a far end 114. In the illustrated example, the near end 112 depicted as having an optional stress relief sleeve as well as a fluid port 116 for administering fluid through the device 100. The devices can also include an optional source of current for coupling to electrodes on the device 100 (as described below), for pacing the soft tissue, monitoring EKG, determining whether the device's cutting member is embedded within tissue, electrocautery, coagulation and/or electrodeposition of medicines or other substances. Similarly, the device 100 can include one or more sources of fluid 134 for coupling to the device 100 via a fluid port 116. The fluid can be dispensed through the cutting member opening 124 or through a separate opening.

Variation of the device 100 can also include an atraumatic tip 120 that can optionally selected to be radiopaque. Alternatively, or in combination cutting element can be radiodense so it is visible and its position can be determined during use. The example depicted in FIGS. 1A and 1B includes an atraumatic tip having the shape of a curved elastic member. In those cases, where the device 100 is used in the heart or other cavity the atraumatic curved member 120 protects the tissue from being punctured by the tip of the device 120. The elastic curved member 120 also is able to flex and relax when pushed into the apex of the heart or cavity. In those variations where the flexed tip 120 is radiopaque, a physician performing the procedure will be able to observe the shape change of the tip under fluoroscopic imaging. When physician then actuates the device to cut tissue, the elastic property of the tip 120 pushes far end 114 of the device against tissue and assists in keeping the cutting element or member within the soft tissue while the cut is being made. Such a feature is especially useful when cutting heart tissue and the heart muscle is contracted during systole. Optionally, the device 120 can augment the process by pacing, of tissue using electrical impulses.

FIG. 2A illustrates perspective partial cross sectional view of a far end 114 of the device 100 of FIGS. 1A and 1B. In this example, the far end 114 of the flexible shaft includes a relatively rigid section 122 coupled to the shaft 110. The rigid section 122 carries a cutting member 140 that is secured to the rigid section 122 using a pivot member 144. The cutting member 140 depicted is for illustration purposes only. Any number of blade shapes can be employed in addition or in combination with the illustrated cutting member. The cutting member 140 is also coupled to a link member 148 at a connection point 150. The link member 148 extends through the shaft 110 and is secured to the actuating member 106 discussed above. The link 148, a wire in the illustrated example, can include additional components to assist in applying a tensile force to the cutting member 140. In the illustrated example, the link member 148 includes an inner tube 152 and an outer tube 154 that are located within a passage 118 of the flexible shaft 110. Such components can improve the structural integrity of the link 148 or can serve to insulate and/or separate the link 148 from electrical components (not illustrated) extending through the passage 118. The passage can also include a valve either in the shaft and/or in the handle continuous to prevent back bleeding into the catheter. A channel for a guide wire can also be used.

Figure 2B:
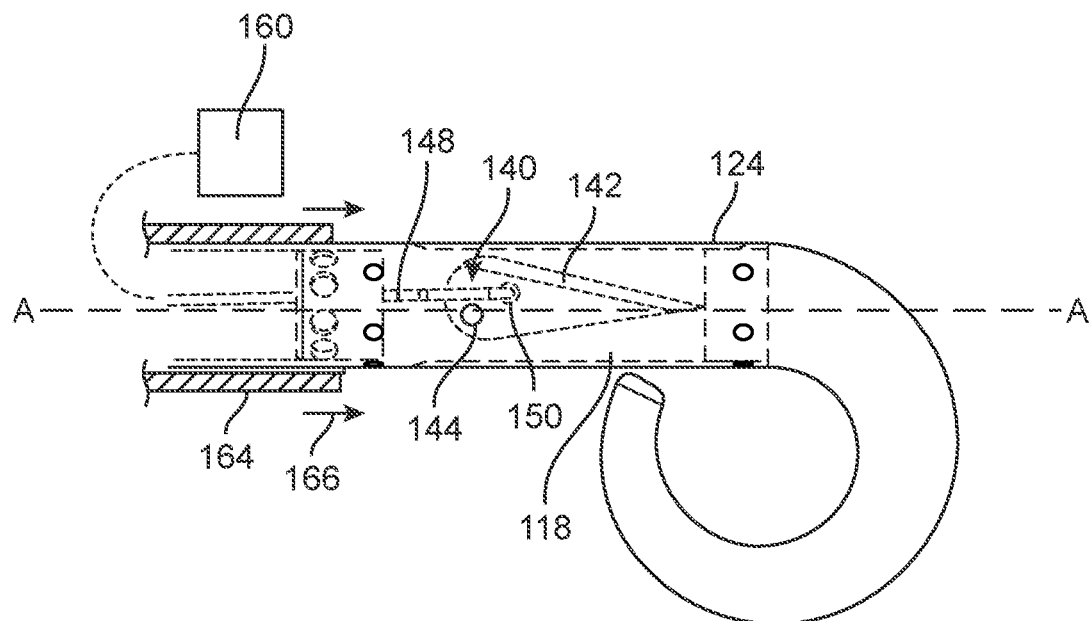
FIG. 2B illustrates a partial side view of the device above showing the link being secured between the actuating member and cutting member.

FIG. 2B illustrates a partial side view of the device 100 discussed above, as shown the link 148 is secured to the actuating member 106 (shown in FIGS. 1A and 1B) such that upon application of a tensile force, the link member 148 causes movement of the cutting member 140. However, prior to actuation, the cutting member 140 is retained within the device 100 so that the cutting surface 14 is shielded and cannot inadvertently cut tissue. Variations of the device can also include additional features 160 can be coupled to the cutting member 140 and/or the link 148 such as a strain gauge, spring, or similar structures that allow either retention of the cutting member within the device 100 or monitoring of the cutting member 140 as it cuts tissue. As illustrated, a variation of the device 100 includes a cutting member 140 having a link connection point 150 that is offset from an axis A-A of an area of the device 100 immediately surrounding the cutting member. This eccentric configuration improves actuation of the cutting member and can cause the far end of the device 100 to preferentially apply a force toward a lateral side of the device where the cutting edge 142 is eventually exposed. Such a feature can increase the ability and ease of which the physician can push the cutting edge 142 into the heart muscle. In additional variations, the entire cutting assembly 140 (including the pivot point 144) is offset from the axis towards the lateral side of the device 100.

FIG. 2B also illustrates an optional sheath 164 or cover that can be slidably mounted on the flexible shaft 110. During advancement or positioning of the device, the sheath 164 can be advanced over the opening 124 to prevent the cutting member 140 from inadvertently damaging tissue. Moreover, the sheath 164 can function as an added safety measure since distal movement (in the direction of arrows 166 can separate the cutting member from tissue or can push the cutting member back into the device 100 if the link 148 fails.

Figure 2C:
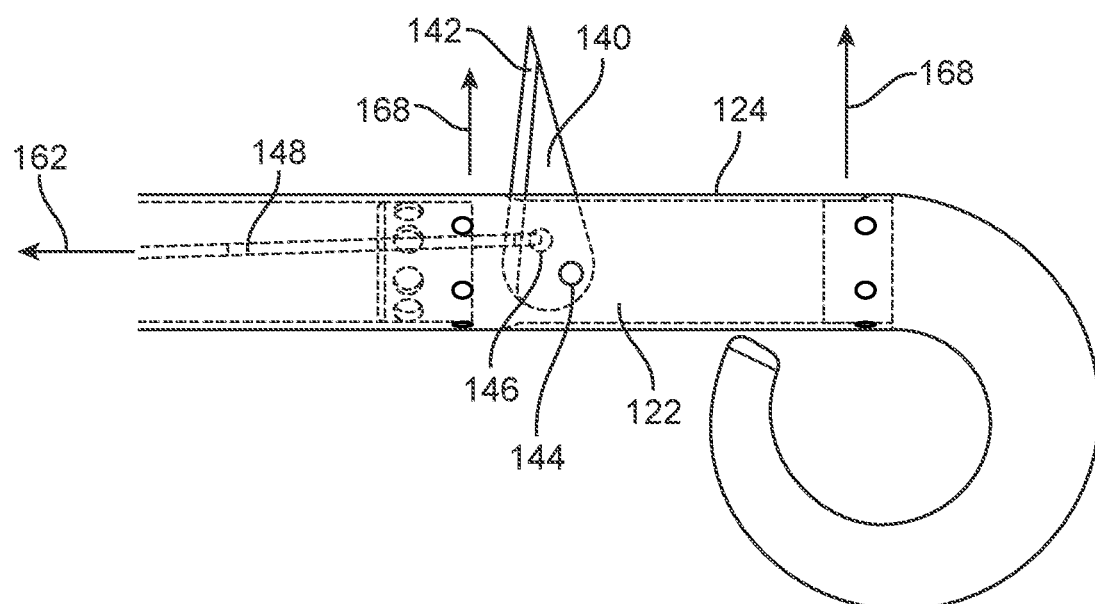
FIG. 2C illustrates a proximal or tensile force applied to the link causing the cutting member to pivot out of the opening towards a lateral side of the device.

FIG. 2C illustrates a proximal or tensile force 162 applied to the link 148 causing the cutting member 140 to pivot out of the opening 124 towards a lateral side of the device 100. In the illustrated variation, the cutting edge 142 is exposed in a rearward direction so that pulling on the device 100 allows the cutting member 140 to cut tissue when the cutting member is advanced adjacent to or positioned within tissue. As noted above, the main passage 118 of the device (or any additional lumen or fluid supply tube) can be used to deliver any number of fluids or substances to an opening in the device, including but not limited to the cutting member opening 124.

In alternate variations, the cutting member 140 includes cutting edges 142 on the front side or on both sides of the cutting member 140 to allow rearward and forward cutting. FIG. 2C also illustrates the link 148 being eccentric in relation to an axis of the device. This feature results in a lateral force component as noted by arrows 168. The lateral force component 168 is directed towards the lateral side of the device and assists in maintaining the cutting member 140 within tissue during cutting. As noted above the lateral force causes the catheter to differentially bend or urges the Far end of the device 100 toward the blade side (lateral side), increasing the ability to push the blade into the heart muscle or other soft tissue. Additional variations of the device do not rely upon eccentric placement of the cutting member or link but create a lateral force through adjustment of the blade configuration. In addition, variations of the device include a pivot 144 that is located distally to the link attachment point 146 when the cutting member 140 is exposed. As shown in FIG. 2C, the link attachment point 146 is proximally located relative to the pivot 144. This configuration prevents interference between the link 148 and the pivot 144 of the cutting member 140 and allows the link to apply lateral force to the far end of the device so that the device flexes in the direction of the cutting member 140.

As noted above, a variation of the device 100 can include the cutting member 140 that is positioned within a rigid section 122 that is adjacent to the flexible shaft 110. The rigid section prevents deflection of the area adjacent to the cutting member opening 124, which allows for greater control of the amount of exposure of the cutting edge.

Figure 3A:
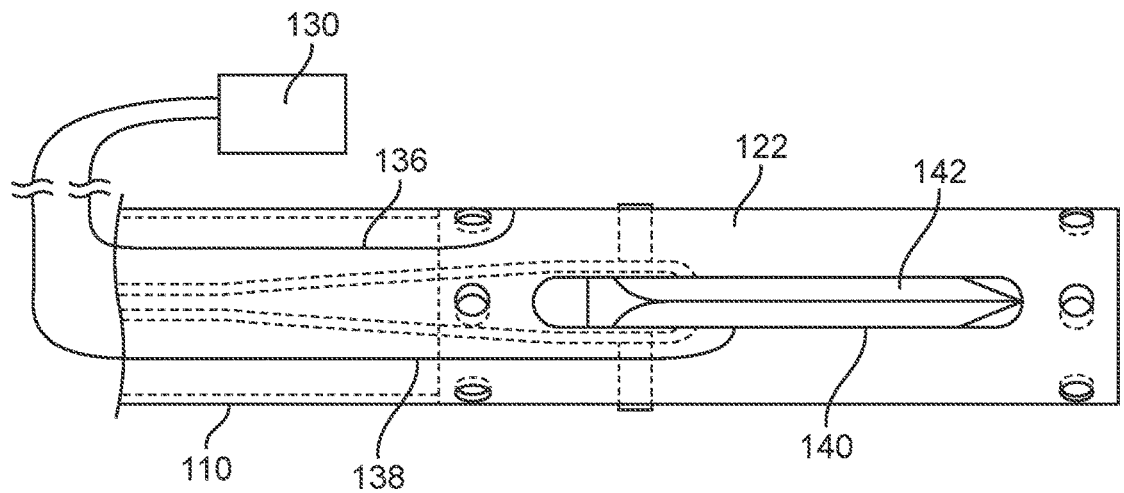
FIG. 3A illustrates a variation of the device where a rigid section of the flexible shaft comprises an enclosure that is secured to a distal end of the flexible shaft.

FIG. 3A illustrates a variation of the device where the rigid section 122 comprises an enclosure that is secured to a distal end of the flexible shaft 110. The enclosure 122 can comprise a conductive material so that it can be used to apply energy, pace tissue, or sense for contact with tissue. In such a case, the enclosure can be electrically coupled to a power supply 130 via known means 136. Alternatively, the enclosure can comprise an insulated or non-conductive structure but still selected to maintain rigidity as described above.

Alternatively, or in combination, the cutting member 140 can be selected from a conductive material and electrically coupled to a power supply 138 via known means. In additional variations, the cutting member 140 can be fabricated from a non-conducting material or insulative material (e.g., ceramic, polymer, a composite material). In the latter case, the cutting member 140 can optionally include one or more electrodes or energy transfer surfaces that are affixed or positioned on one or both sides of the cutting member 140.

Figure 3B:
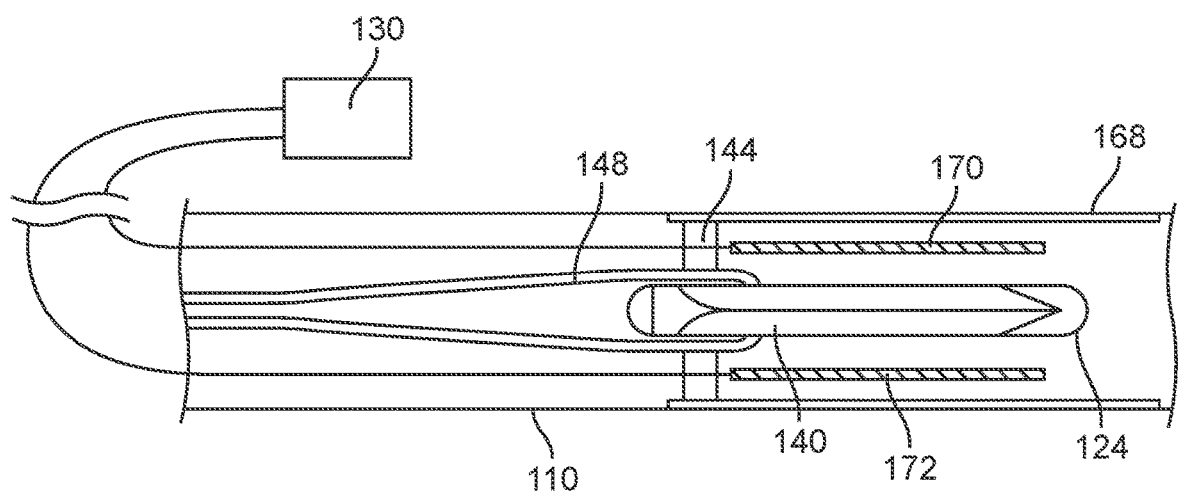
FIG. 3B shows a variation where the flexible shaft houses the cutting member with a reinforcement member (either external or internal to the shaft) coupled to the flexible shaft where the reinforcement member renders the area as a rigid section.

In an additional variation, as shown in FIG. 3B, the flexible shaft 110 can house the cutting member 140 in such a case, a reinforcement member 168 (either external or internal to the shaft 110) can be coupled to the flexible shaft 110 where the reinforcement member renders the area as a rigid section.

FIG. 3B also illustrates a variation of the device where the flexible shaft 110 includes one or more electrodes 170, 172 on an exterior of the shaft 110 and adjacent to the opening 124. As shown, the electrodes can be coupled to a power supply using known means. The electrode configuration can be employed on the enclosure shown in FIG. 3A as well.

Figure 4A:
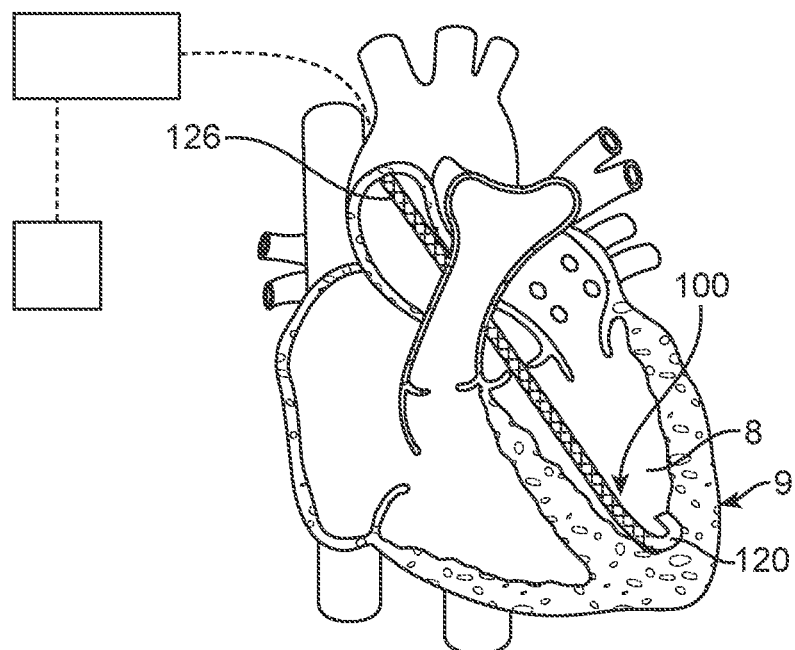
FIGS. 4A to 4C illustrate advancement of a device into a heart to create a lesion as described herein.

FIG. 4A illustrates an example of a treatment device as described herein being used in a chamber of the heart 9. Clearly, the device 100 can be used in any pocket or cavity of soft tissue. As illustrated, a physician advances a treatment device 100 into a chamber 8 of the heart 9. Once inside the chamber 8, in this example the left ventricle, the physician can advance an atraumatic tip 120 of the device 100 against tissue (in this case the apex of the chamber) to provide an opposing force to allow penetration of the cutting member into cardiac tissue. Because the atraumatic tip 120 is elastic and resilient there is a reduced risk that the tip 120 will create undesired injury. In addition, the flexible shaft of the device 100 can include any number of reinforcing member 126 such as braids, coils, polymer coextrusion, etc., that maintains torqueability and/or column strength of the flexible member. Such characteristics are required for accurate placement of the cutting element against the desired area of tissue. As noted above, electrodes (or components of the device) can be used with a power supply 130 to assist in placement of the device, and/or provide therapeutic treatment. In some variations the device can be configured as a bi-polar device, with electrodes of opposite polarity on the device. Alternatively, the device can function in a monopolar or unipolar configuration. In such a case an external electrode 131 can be positioned on a remote area of the patient's body.

Figure 4B:
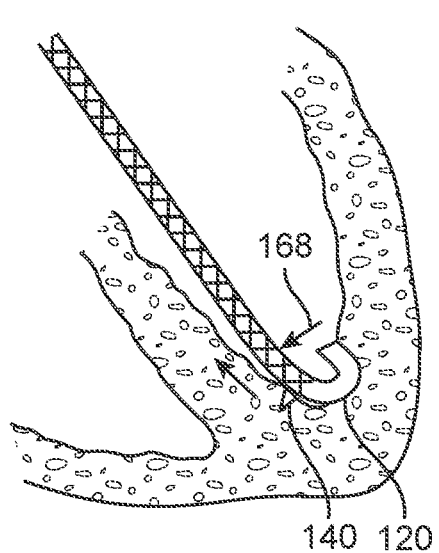

FIG. 4B shows a magnified view of the device 100 being advanced into position at the apex of the heart where deformation of the atraumatic tip 120 applies a force in a lateral direction 168. As noted above, the atraumatic tip 120 is not limited to a curved configuration; instead, any shape that delivers a biasing force can be employed. Furthermore, some variations of the device may not require a biasing force applied by the tip.

Figure 4C:
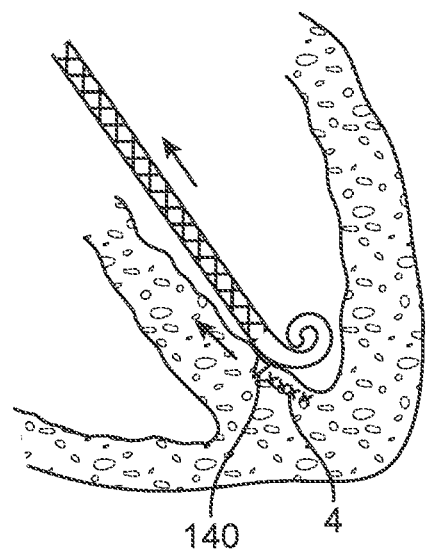

FIG. 4B also illustrates advancement of the cutting member 140 to the lateral side. As noted above, this action can also apply a lateral force to assist in placement of the cutting element 140 within tissue. As shown in FIG. 4C, The lateral force can assist retention of the cutting element 140 as it is withdrawn in a proximal or rearward direction leaving the therapeutic cut 4 in tissue. As noted above, a strain gauge or other structure can be used to measure the drag or resistance on the device to assist in determining whether the cutting element is engaged in tissue. In any case, as noted above, tension applied by the link not only actuates the cutting member, but also, when positioned in an eccentric location within the shaft, the tension also causes the catheter to differentially bend toward the blade side, increasing the ability to push the blade into the heart muscle.

Again, the shape of the blade or cutting member can be selected so that it stays in tissue while being pulled. In certain variations, the cutting member opens from distal to proximal direction so that it can be safely closed by retracting into the device sheath or by pushing a sheath over the cutting member.

The cutting element can be an electrically insulated blade (e.g., made of ceramic, polymers, or a composite structure) that allows electrodes on both sides of blade to be electrically isolated from each other. Electrodes can be used to monitor EKG for a current of injury to demonstrate cutting, can be used to pace the heart, demonstrating that the blade is within the heart muscle, and for other uses (electrocautery, depth measurement, electrodeposition of drugs/chemicals). If the cutting element is fabricated from a conductive material, it can be used for pacing, which allows a cut to be made during systole and pushes muscle onto blade for cutting. Alternatively, or in combination, the rigid section of the device can be used as a return electrode for sensing, treatment or manipulation of tissue as discussed above.

As noted above, the depth of cut can be varied by making the blade longer or shorter using the adjustments and stops discussed above. It can also be varied in a given-length blade catheter by exposing more or less blade with the angle of exposure varying from barely out of the catheter to 90 degrees from the long axis of the catheter.

The handle shown in FIGS. 1A and 1B can be ergonomic and allow the cutting element to be exposed by flexing the lingers of the operator's hand, and retracted by extending the fingers. The stop, as discussed above, can be placed on the handle so that the maximum blade exposure can be limited to a preset angle, corresponding to a preset depth. Electrical components can be connected at the handle which is electrically connected to the blade through the pull wire.

In many variations, the tip or cutting edge of the cutting member is sharp enough to allow the heart muscle (or other soft tissue) to be stabbed and the angle between the dull and sharpened side is acute enough to allow cutting with minimal force. An alternative sickle-shape is also possible, which causes the blade to remain within the tissue while being pulled but requires the knife to be pushed backward after the cut to disengage the tissue.

The device can also employ a pull-apart or splittable cover that retains the curved atraumatic tip temporarily straight to allow for easy entry into a guiding sheath during use. When this pull-apart cover is pulled off, the curled, tip bends once it is unconstrained by the guiding sheath. This makes for ease of use, but also ensures single-use.

The diameter of the catheter does not constrain the length of blade or depth of cut as the width of the blade can be reduced to fit within even a small catheter. The length of the blade can therefore be several times the diameter of the catheter. For example, in one example the diameter of the device was 7 French, allowing, it to go through the smallest of guide catheters known.

Figure 5A:
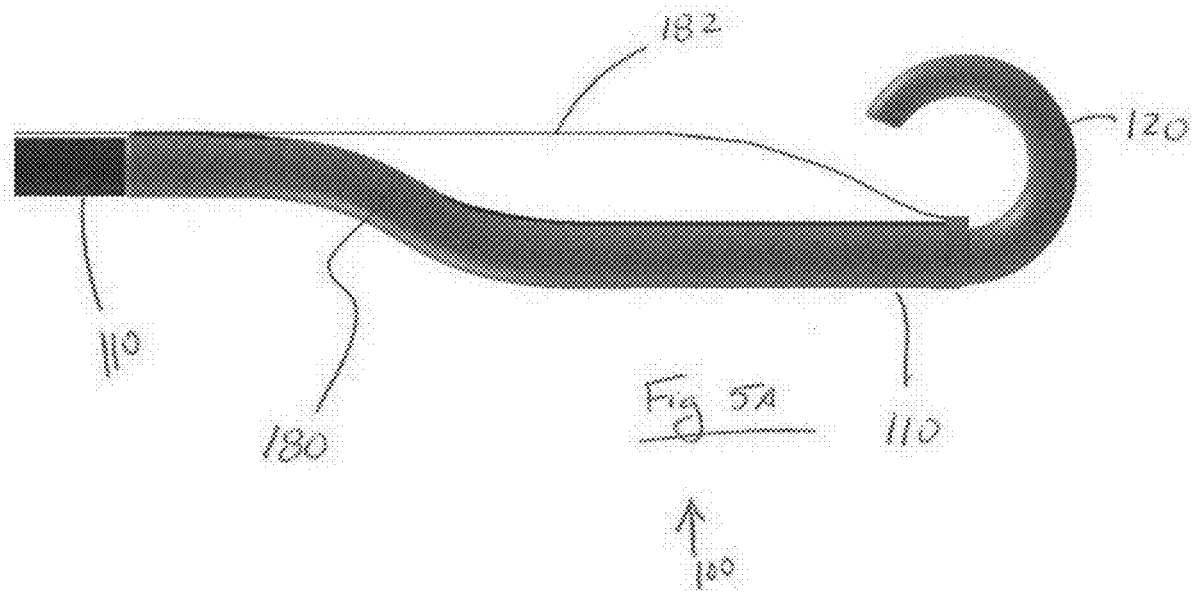
FIGS. 5A and 5B illustrate an additional variation of a medical configured for advancement into a heart to create a lesion as described herein.
Figure 5B:
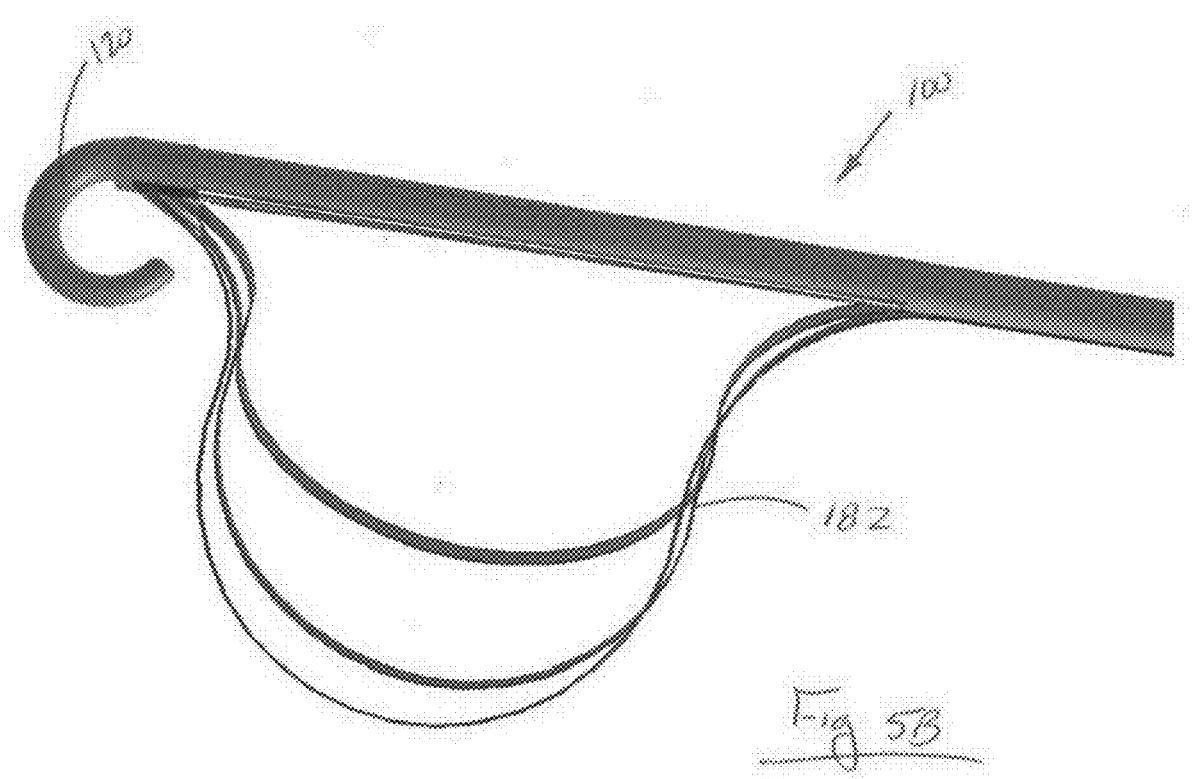

FIGS. 5A and 5B illustrate an additional variation of a medical device 100 configured to perform the procedures discussed herein. In this example, the medical device 100 includes features useful to direct the cutting element (not shown) against a wall of tissue when the opening into the cavity or heart is offset from the wall of tissue. As shown, the device 100 can include an of et 180 or bend that positions a cutting side of the device away from an axis of the proximal portion of the shaft 110. The offset 180 can be shape set or activated/actuatable. The illustrated device 100 of FIG. 5A can also optionally include one or more strut members 182 that further provide a biasing force on a side of the device 100 opposite to the cutting member. FIG. 5B illustrates a variation of the device 100 including three struts 182. The devices described herein can include any number of struts 182 where the struts can be located circumferentially away from the cutting member to provide a biasing force against an opposing wall of tissue, such that the opposing force assist in maintaining the cutting element within tissue.

FIG. 5C illustrates a variation of a strut 182 assembly that is positionable in the shaft of the device at the working end/far end. In use, the first end 184 is moveable relative to the second end 186 to permit outward flaring or deflection of the struts 182. In addition, the end 168 of the strut can include features to improve bonding of the strut assembly to the shaft of the device.

Figure 6A:
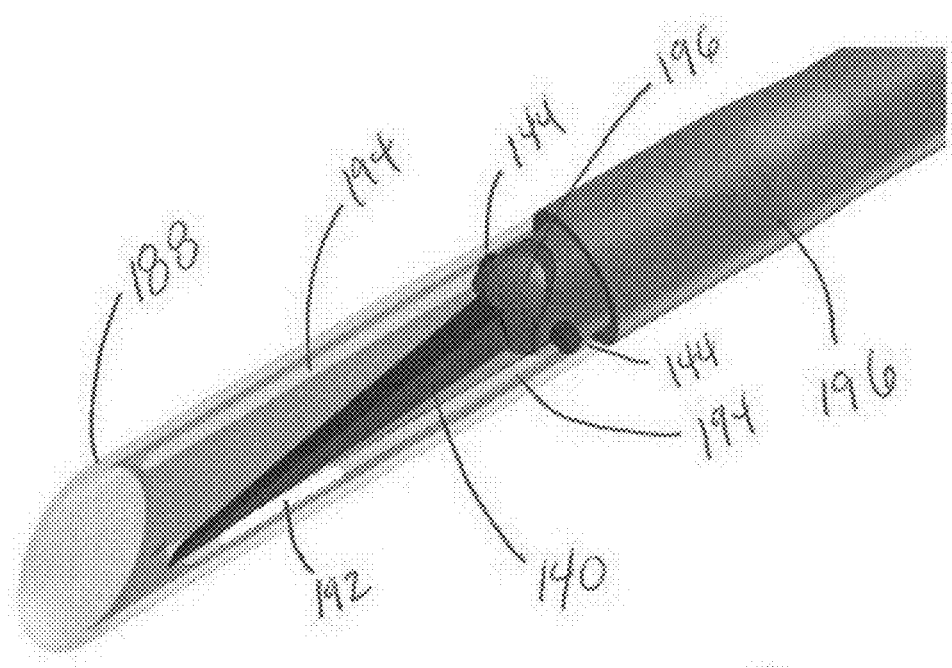
FIGS. 6A and 6B illustrate another variation of a device with orientation features to ensure positioning of the cutting side/opening with respect to the device.
Figure 6B:
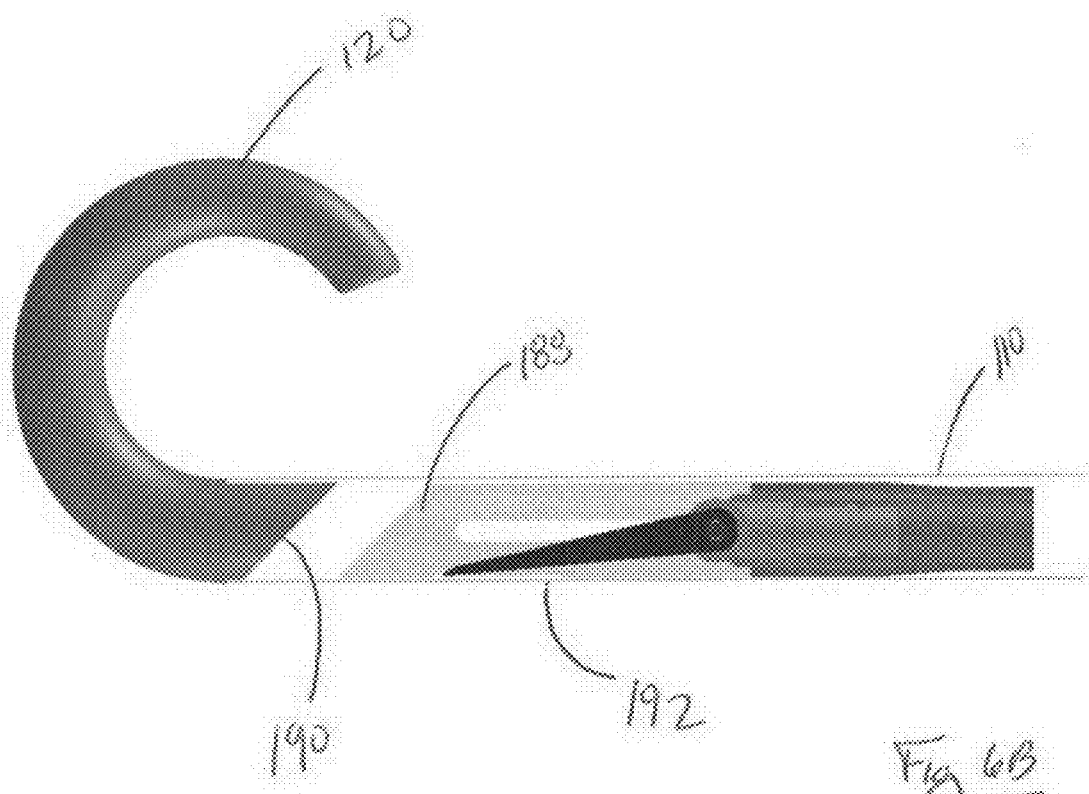

FIGS. 6A and 6B illustrate another variation of a device for use as described herein, where the device includes orientation features to ensure positioning of the cutting side/opening 192 with respect to the device. As shown in FIG. 6A, the cutting assembly can include a cutting member 140 coupled to a shaft 196 where a distal portion of the cutting assembly includes an alignment feature 188. As shown in FIG. 6A, the cutting assembly is advanced within a shaft 110 of the device to permit actuation of the cutting member 140. The alignment feature 188 of the cutting assembly can be configured to nest against an alignment feature 190 of the device. In the illustrated variation, the alignment feature of the device 190 is positioned on the flexible tip 120, however, any number of alignment features are within the scope of this disclosure as long as the alignment feature(s) permit registration/orientation of the cutting element to a pre-determined side of the device. The illustrated example also permits continued closing movement of the alignment features 188 and 190 to naturally bias the orientation of the cutting assembly towards the desired orientation.

One added benefit of such a configuration is that the length of the cutting shaft 196 can be marked or have a specific length such that the user can observe the proximal end of the cutting shaft 196 in relation to a proximal end of the device or shaft 110 to identity or confirm that the alignment features 188 and 190 are properly nested together.

FIGS. 6A and 6B also illustrate a variation of the cutting element 140 coupled to a base 196 that includes pins 144 that ride in slots 194 of the cutting assembly. Where relative motion between the cutting shaft 196 and the shaft 110 of the device permits actuation of the knife.

The methods described herein can be performed using a number of additional modes to determine proper placement. For example, the methods can be performed under fluoroscopy and/or with contrast agents. Alternatively, or in combination, a device can include a pressure sensing tip or along catheter at one or multiple points that determine when the device is positioned against the heart wall. In another variation, the device can include an opening at the distal end that is attached to arterial sensing equipment. Next, the waveform of a pressure wave is observed. When the hole is covered by tissue, the tissue blunts the waveform. This effect can be used as a test for catheter wall apposition. A physician can also confirm placement using, an echocardiogram (TTE, TEE, intracardiac) where image shows position of device relative to wall/tissue.

Current can also be used to determine blade contact with tissue. For example, a current can be placed through the tissue (through ekg or similar type electrochemical sensing). As the blade touches the tissue, a voltage change can be measured from the circuit completed by the blade's contact with tissue.

Additionally, implantable hardware within, near, or around these cuts/holes with drug eluting capability may be part of this procedure. As well, the hardware (knife or otherwise) used to make the intervention on the cardiac chambers may be coated with drugs much like in drug coated balloon angioplasty.

As noted herein, the physician can create one or more therapeutic incisions, cores, holes, or other similar therapeutic damage to increase volume in the ventricle when in diastole. As noted above, this damage reduces the stiffness of the ventricle (or cardiac muscle in the wall) to improve ventricular filling and reduce diastolic filling pressure (which resists blood flow into the ventricle). The method includes making one or more therapeutic damage sites within one or more chambers of the heart. In this variation, the treatments occur in the endocardium 2. Any of the treatment devices 3 described herein can include spring biasing, steering, a steerable sheath or catheter, a pull wire, or other mechanism to assist in navigation or apposition of the working end 4 of the device 3 against the target site.

Devices for use in the methods described herein can incorporate alternative design options to improve safety to critical structures and to ensure cuts are made as expected (any combination or singular use of the below may be incorporated with any of the variations of the methods or devices discussed herein.)

The devices described herein can be used in other applications as well. For example, devices have application to make MAZE incisions by making multiple cuts in or around the pulmonary veins to interrupt conduction of atrial electrical activity. The devices and procedures can be used for commisurotomy, by cutting valve in various places including commissures to decrease valvular stenosis. The devices can be used for any and all cardiovascular structures that have undergone stenosis/sclerosis, such as renal arteries/pulmonary veins after RF exposure by cutting longitudinally with knife catheter. Furthermore, the devices can be used to perform plastys in all chambers of the heart by cutting longitudinally with the knife blade, Another potential use includes septal ablations by cutting longitudinally with the knife device; endarterectomy using the blade as cutting device to remove plaque. This peeling/cutting device will be proximal to a distal umbrella unit at the tip of the device that is used to both peel plaque and prevent embolization. Current open methods of carotid endarterectomy lead to stenosis secondary to opening the vessel and subsequently closing the incision; our method would provide an advantage over this as we would not be opening the vessel. Glaucomaplasty via Canal of Schlem incision thus increasing the diameter of the canal, increasing the flow of aqueous humor, and thus decreasing intraocular pressures. The devices can be used for tear duct plasty as well as looking for chronic sinusitis; third ventriculoplasty for obstructive hydrocephalus; and psialalithiasis intervention to remove stones.

I claim:

1. A medical device for creating elongated incisions within soft tissue, the device comprising:
    a handle comprising a handle body and an actuating member;
    a flexible shaft having a near end coupled to the handle body and a far end;
    an atraumatic tip located at the far end;
    a cutting member pivotally secured within the flexible shaft and having a cutting edge;
    a linking member coupling the actuating member of the handle to the cutting member, wherein when the actuating member applies a tensile force to the linking member, the cutting member pivots to a lateral side of the flexible shaft to expose the cutting edge and allow cutting of the soft tissue wherein the cutting member pivots about a pivot point that does not move axially relative to the shaft assembly, the tensile force also causing biasing of the far end of flexible shaft towards the lateral side to assist in maintaining the cutting edge within the soft tissue; and
    at least one strut that extends away from the flexible shaft on a side of the shaft opposite to the cutting member, such that the strut provides a biasing to assist in maintaining the cutting edge within the soft tissue.

2. The medical device of claim 1, further comprising a channel extending between the near end of the flexible shaft through the opening.

3. The medical device of claim 1, where the linking member is offset from a pivot point of the cutting member.

4. The medical device of claim 1, further comprising a sheath being slidably located on the flexible shaft, where the sheath can be advanced to cover the opening and retracted to expose the opening.

5. The medical device of claim 1, where the cutting member comprises an electrically non-conductive material.

6. The medical device of claim 5, further comprising at least one electrode located on the electrically non-conductive material, where the at least one electrode is electrically coupleable to a source of electrical current.

7. The medical device of claim 1, where the cutting member comprises an electrically conductive material and where the cutting member is electrically coupleable to a source of electrical current.

8. The medical device of claim 1, further comprising an opening adjacent to the far end of the flexible shaft, where the cutting edge of the cutting member extends through the opening when pivoted.

9. The medical device of claim 8, further comprising an electrode adjacent to the opening.

10. The medical device of claim 1, further comprising a rigid section at the far end of the flexible shaft where the rigid section comprises an opening through which the cutting edge of the cutting member extends when pivoted.

11. The medical device of claim 10, where the rigid section comprises a conductive material and is coupleable to a source of current.

12. The medical device of claim 10, where the rigid section comprises a metal enclosure.

13. The medical device of claim 10, where the cutting member is located within the rigid section and configured to pivot.

14. The medical device of claim 1, further comprising a strain measurement device coupled to the linking member.

15. The medical device of claim 1, wherein the linking member is offset from an axis of the flexible shaft to assist in biasing the far end of the flexible shaft upon application of the tensile force.

16. The medical device of claim 1, where the atraumatic tip comprises a curved elastic member.

17. The medical device of claim 1, where the atraumatic tip is radiopaque.

18. The medical device of claim 1, where the cutting member is releasably fixable upon pivoting to the lateral side such that the cutting member is adjustable between a range of angles relative to the flexible shaft, where the range of angles can be varied to adjust a cutting depth in the soft tissue.

19. The medical device of claim 18, further comprising a stop coupled to the linking member, where the stop limits pivoting of the cutting member.

20. The medical device of claim 1, where the flexible shaft further includes a braid such that to improve rotational stiffness of the flexible shaft.

21. The medical device of claim 1, where the flexible shaft further includes a guidewire lumen.

\* \* \* \* \*